(12) United States Patent
Bonneau

(10) Patent No.: US 6,194,143 B1
(45) Date of Patent: Feb. 27, 2001

(54) SUBSTRATES FOR HUMAN CYTOMEGALOVIRUS PROTEASE

(75) Inventor: Pierre R. Bonneau, Blainville (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 0 days.

(21) Appl. No.: 09/171,590

(22) PCT Filed: Dec. 23, 1997

(86) PCT No.: PCT/CA97/01003

§ 371 Date: Oct. 20, 1998

§ 102(e) Date: Oct. 20, 1998

(87) PCT Pub. No.: WO98/29562

PCT Pub. Date: Jul. 9, 1998

Related U.S. Application Data (60) Provisional application No. 60/033,854, filed on Dec. 27, 1996.

(51) Int. Cl.$^7$ ................................... C12Q 1/70
(52) U.S. Cl. ................ 435/5; 435/23; 435/24; 530/326; 530/327; 530/328; 530/329; 530/330
(58) Field of Search .................. 435/5, 23, 24; 530/326, 327, 328, 329, 330

(56) References Cited

U.S. PATENT DOCUMENTS 5,506,115    4/1996   Toth .

FOREIGN PATENT DOCUMENTS 0 493 770A2   8/1992   (EP) .
WO96 35806   11/1996   (WO) .

OTHER PUBLICATIONS

Christopher Pinko, Single–chain Recombinant Human Cytomegalovirus Protease, Journal of Biological Chemistry, vol. 270, No. 40, Oct. 6, 1995, pp. 23634–23640.

*Primary Examiner*—Ali R. Salimi
(74) *Attorney, Agent, or Firm*—Robert P. Raymond; Alan R. Stempel; Mary-Ellen M. Devlin (57) ABSTRACT

Human cytomegalovirus (HCMV) protease is a slow-processing enzyme in vitro. Disclosed herein are improved fluorogenic and radiometric peptide substrates for CMV protease. The improved substrates have a Tbg-Tbg-Asn (NMe$_2$) sequence replacing the Val-Val-Asn sequence, corresponding to the $P_4$-$P_2$ residues of the maturation site of the enzyme. The incorporation of this new sequence in a variety of substrates has afforded substrates with improved kinetic parameters compared to homologues containing the natural sequence only. For example, the substrate 2-aminobenzoyl-Tbg-Tbg-Asn(NMe$_2$)-AlaiSer-Ser-Arg-Leu-Tyr(3-NO$_2$) ARG-OH displayed a $k_{cat}/K_m$ value of 15940 M$^{-1}$—s$^{-1}$, i.e. over 60-fold greater than that of the equivalent, non-optimized substrate in identical conditions. The new substrates find use in assays which can evaluate and characterize HCMV protease inhibitors having low nanomolar potency.

26 Claims, 1 Drawing Sheet

FIGURE 1

SUBSTRATES FOR HUMAN CYTOMEGALOVIRUS PROTEASE

This application is based on International Application No. PCT/CA97/01003, filed Dec. 23, 1997, and claims the benefit of U.S. Provisional Application No. 60/033,854, filed Dec. 27, 1996.

FIELD OF THE INVENTION

This invention relates to substrates for herpesvirus proteases, to methods of determining the activity of herpesvirus proteases and to methods of identifying inhibitors of herpesvirus proteases.

BACKGROUND OF THE INVENTION

Herpesviruses inflict a wide range of diseases against humans and animals. For instance, herpes simplex viruses, types 1 and 2 (HSV-1 and HSV-2), are responsible for cold sores and genital lesions, respectively; varicella zoster virus (VZV) causes chicken pox and shingles; Epstein-Barr virus (EBV) causes infectious mononucleosis; and the human cytomegalovirus (HCMV, a β-herpesvirus) is a serious pathogen in immunocompromised individuals, including AIDS patients, neonates and organ transplant recipients {Mocarski, E. S. (1996) in Virology (Fields, B. N., Knipe, D. M., Howley, P. M., Eds.), pp. 2447–2492, Lippincott-Raven Publishers, Philadelphia; and Britt, W. J., Alford, C. A. (1996) in Virology (Fields, B. N., Knipe, D. M., Howley, P. M., Eds.), pp. 2493–2523, Lippincott-Raven Publishers, Philadelphia}. The most widely used antiherpes agents to date are acyclovir and ganciclovir (purine and pyrimidine nucleoside analogs) and foscarnet. These agents have found only limited success in treating herpesvirus infections, and safer and more effective treatment agents are required.

As a member of the Herpesvirus family, HCMV encodes a unique serine protease which is involved in capsid assembly and essential for the production of infectious virions (Preston, V. G., Coates, J. A. V., Rixon, F. J. (1983) *J. Virol.* 45, 1056–1064; Gao, M., Matusick-Kumar, L., Hurlburt, W., DiTusa, S. F., Newcomb, W. W., Brown, J. C., McCann, P. J., III, Deckman, I., Colonno, R. J. (1994) *J. Virol.* 68, 3702–3712; Matusick-Kumar, L., McCann, P. J., III, Robertson, B. J., Newcomb, W. W., Brown, J. C., Gao, M. 1995 *J. Virol.* 69, 7113–7121; Gibson, W., Welch, A. R., Hall, M. R. T. (1995) *Perspect. Drug Discovery Des.* 2, 413–426; and Liu, F., Roizman, B. (1991) *J. Virol.*, 65, 5149–5156). This enzyme is responsible for the processing of the assembly protein whose function is analogous to that of the "scaffolding" protein of bacteriophages {Casjens, S., King, J. (1975) *Annu. Rev. Biochem.* 44, 555–611). Failure to process the assembly protein results in accumulation of only aberrant, non-infectious capsids (Preston, V. G. et al., vide infra). This protease therefore represents an attractive target for the development of new antiviral agents.

In order to identify inhibitors of herpesvirus proteases, assays that allow the measurement of protease activity are required. Initial assays were based on the electrophoretic separation of the cleavage products (Gibson, W. et al., vide infra and Liu, F. et al., vide infra). However, these assays were very slow and cumbersome. More rapid and high-throughput assays using fluorogenic substrates for the HCMV protease were subsequently developed (Holskin, B. P., Bukhtiyarova, M., Dunn, B. M., Baur, P., de Chastonay, J., Pennington, M. W. (1995) *Anal. Biochem.* 227, 148–155; Pinko, C., Margosiak, S. A., Vanderpool, D., Gutowski, J. C., Condon, B., Kan, C.-C. (1995) *J. Biol. Chem.* 270, 23634–23640; Handa, B. K., Keech, E., Conway, E. A., Broadhurst, A., Ritchie, A. (1995) *Antivir. Chem. Chemother.* 6, 255–261; and Toth, M. V., Wittner, A. J., Holwerda, B. C., U.S. Pat. No. 5,506,115 issued Apr. 9, 1996}. These fluorogenic substrates are based on the maturation cleavage site of the enzyme (the "M-site") and exploit the spectral overlap properties of fluorescent donor/acceptor pairs such as EDANS/DABCYL and 2-aminobenzoic acid/3-nitrotyrosine {Matayoshi, E. D., Wang, G. T., Krafft, G., Erickson, J. (1990) *Science* 247, 954–958; and Meldal, M., Breddam, K. (1991) *Anal. Biochem.* 195, 141–147}. The separation between the pair in these HCMV protease substrates varies from 10 to 11 amino acids and the specificity constant, $k_{cat}/K_m$, ranges from 800 to 3000 $M^{-1}s^{-1}$ (Table I).

TABLE I

PRIOR REPORTS OF HCMV PROTEASE FLUOROGENIC SUBSTRATES

| Substrate | $k_{cat}$ ($s^{-1}$) | $k_M$ ($\mu M$) | $k_{cat}/K_M$ ($M^{-1}s^{-1}$) |
|---|---|---|---|
| DABCYL-RGVVNA-SSRLA-EDANS[a] | nd | nd | 796 |
| DABCYL-RRVVNA-S-Aba-RLD(EDANS)-NH$_2$[b] | nd | 3.0 | nd |
| ABz-GVVNA-SSRLAY(3-NO$_2$)G[c] | 0.37 | 134 | 2750 |
| Y(3-NO$_2$)GVVNA-SSRLA-ABz-K[c] | nd | nd | 3167 |

[a]Holskin, B. P., Bukhtiyarova, M., Dunn, B. M., Baur, P., de Chastonay, J., Pennington, M. W. (1995) Anal. Biochem. 227, 148–155.
[b]Handa, B. K., Keech, E., Conway, E. A., Broadhurst, A., Ritchie, A. (1995) Antivir. Chem. Chemother. 6, 255–261
[c]Pinko, C., Margosiak, S. A., Vanderpool, D., Gutowski, J. C., Condon, B., Kan, C. -C. (1995) J. Biol. Chem. 270, 23634–23640.

These numbers reflect both the extensive requirement of herpesvirus proteases for a long peptide chain and their relatively low activity compared to other viral proteases (Gibson, W. et al., vide infra).

As disclosed herein, a new class of substrates, modeled on the maturation site of the enzyme, has been developed. The kinetic properties of the new substrates of this class are suitable for the elaboration of, for example, a fluorometric, chromogenic or radiometric assay for screening and mechanistic studies of HCMV protease inhibitors. If one is to achieve rapid progress in the rational design of peptide-based inhibitors, a more active substrate than those found in prior reports is required. The benefits accruing to a more active substrate are a significant reduction of enzyme concentration in the assay and the allowance of an unequivocal determination of inhibitor potency. The requirement of improved activity has now been met by the new substrates disclosed herein.

These new substrates are specifically useful for high performance liquid chromatography (HPLC), radiometric, chromogenic and fluorometric-based assays. The latter type of assay usually offers significant advantages over the other approaches, such as greater throughput, higher sensitivity and continuous monitoring of the hydrolytic process. Most recently, the growing interest in the design of new fluorogenic substrates is exemplified by their numerous application in a variety of enzymatic protocols {Matayoshi, E. D. et al.,vide infra; Wang, G. T., Chung, C. C., Holzman, T. F., Krafft, G. A. (1993) *Anal. Biochem.* 210, 351–359; Pennington, N. W., Zaydenberg, I., Byrnes, M. E., de Chastonay, J., Malcolm, B. A., Swietnicki, W., Farmerie, W. G., Scarborough, P. E., Dunn, B. M. (1993) in Peptides 1992: Proceedings of the 22nd European Peptide Symposium (Schneider, C. H., Eberle, A. N., Eds), pp. 936–937, Escom, Leiden, Netherlands; Pennington, M. W., Thornberry, N. A. (1994) *Peptide Res.* 7, 72–76; Knight, G. C. (1995) *Meth. Enzymol.* 248, 18–34 (and references therein); and Jean, F., Basak, A., DiMaio, J., Seidah, N. G., Lazure, C. (1995), *Biochem. J.* 307, 689–695}.

SUMMARY OF THE INVENTION

One aspect of this invention involves a substrate, suitable for cleavage by a herpesvirus protease, represented by formula I:

X-Tbg-Tbg-Y-Ala-Z (I) [SEQ ID NO:1]

wherein X is a fluorescent donor radical, a fluorescent acceptor radical, an affinity tag, a detectable label or an N-terminal capping group; or X is an amino acid sequence, or derivative thereof, sufficient for substrate recognition and to which a fluorescent donor radical, a fluorescent acceptor radical, an affinity tag, a detectable label or an N-terminal capping group, is optionally attached;

Y is a divalent radical $NHCH\{CH_2C(O)N(R^1)(R^2)\}C(O)$ wherein $R^1$ and $R^2$ are independently selected from hydrogen, lower alkyl, lower cycloalkyl or (lower cycloalkyl)-(lower alkyl), or $R^1$ and $R^2$ together with the nitrogen atom to which they are attached form a pyrrolidino, piperidino or morpholino; and Z is an amino acid sequence or derivative thereof sufficient for substrate recognition and to which a fluorescent donor radical, a fluorescent acceptor radical, an affinity tag or a detectable label is optionally attached; or Z is an aromatic amino or phenoxy compound whose fluorescence or absorbance characteristics change upon acylation with an amino acid; or Z is amino, lower alkylamino or lower alkoxy; with the provisos (1) that when one of X and Z comprises a fluorescent donor then the other of X and Z comprises a fluorescent acceptor radical, and (2) that when one of X and Z comprises an affinity tag then the other of X and Z comprises a detectable label; wherein the protease cleaves the substrate at the corresponding amide or ester bond between Ala and Z.

In accordance with another aspect of the present invention there are provided methods of measuring the activity of a herpesvirus protease using the aforementioned substrate.

In accordance with yet another aspect of the present invention there are provided methods of identifying inhibitors of a herpesvirus protease using the aforementioned substrate.

DETAILED DESCRIPTION OF THE INVENTION

In general, the abbreviations used herein for designating the amino acids and the protective groups are based on recommendations of the IUPAC-IUB Commission of Biochemical Nomenclature, see *European Journal of Biochemistry* 138, 9 (1984). For instance, Ala, Arg, Val, Ile, Ser, Tbg, Thr, Tyr, Asn and Leu represent the residues of L-alanine, L-arginine, L-valine, L-isoleucine, L-serine, L-tert-butylglyine, L-threonine, L-tyrosine, L-asparagine and L-leucine, respectively.

The term "fluorescent donor radical", as used herein, means a fluorescence emitting radical which can be modified and attached to the amino acid sequence. Examples of such radicals are those derived from 2-aminobenzoyl (and halogenated derivatives thereof), 5-{(2-aminoethyl)amino}-naphthalene-1-sulfonyl (EDANS), 5-(dimethylamino) naphthalene-l-sulfonyl (DANSYL), 7-methoxycoumarin-4-acetyl, nicotinic acid (and derivatives thereof) and tryptophan.

The term "fluorescent acceptor radical", as used herein, means an aromatic quenching radical which absorbs the fluorescence energy of the fluorescence donor radical and reduces the fluorescence emission when the fluorescence donor radical is covalently attached in close proximity to the acceptor radical. Examples of such radicals include 3-nitrotyrosine, 4-nitrophenylalanine, 2,4-dinitrophenylalanine, DANSYL, 4-{{4-(dimethylamino) phenyl}azo}benzoyl (DABCYL) or 4-(dimethylamino) azobenzene-4'-sulfonyl (DABSYL).

The term "affinity tag", as used herein, means a ligand whose strong affinity for a receptor can be used to extract from a solution the entity to which the ligand is covalently attached. Examples of such ligands include biotin or a derivative thereof, an histidine polypeptide, an amylose sugar moiety or a defined epitope recognizable by a specific antibody.

The term "detectable label", as used herein, means an atom or a radical whose physical properties or interactions with other molecules permit sensitive detection of its presence by radioactive or chromogenic measurements.

The term "capping group", as used herein, means a group replacing a hydrogen on the N-terminal nitrogen of an amino acid or peptide. The group has the effect of preventing further chemical reactions from occurring at that site until the capping group is ultimately removed. Example of capping groups include acetyl and succinimidyl.

The term "aromatic amino radical", as used herein means a radical derived from an aromatic amine by the removal of a hydrogen from the amino group; the aromatic amine having fluorescence or absorbance properties which change upon acylation of the amino group. Examples of aromatic amines include 7-amino-4-methylcoumarin, 6-amino-1-naphthalenesulfonamine, rhodamine 110 (Aldrich Chemical Co., Milwaukee, Wis., USA), 2-naphthylamine, 4-methoxy-2-naphthylamine and nitroaniline.

The term "phenoxy radical", as used herein, means a radical derived from a phenolic compound by the removal of a hydrogen from the hydroxy, the phenolic compound having fluorescence or absorbance properties which change upon acylation of the hydroxyl. Examples of such phenolic compounds include 4-nitrophenol and the like.

The term "lower alkyl" as used herein, either alone or in combination with a radical, means straight chain alkyl radicals containing one to six carbon atoms and branched chain alkyl radicals containing three to four carbon atoms and includes methyl, ethyl, propyl, butyl, hexyl, 1-methylethyl, 1-methylpropyl, 2-methylpropyl and 1,1-dimethylethyl.

The term "lower cycloalkyl" as used herein, either alone or in combination with a radical, means saturated cyclic hydrocarbon radical containing from three to six carbon atoms and includes cyclopropyl, cyclobutyl, cyclopentyl and cyclohexyl.

The term "lower alkoxy" as used herein means straight chain alkoxy radical containing one to six carbon atoms and branched chain alkoxy radicals containing three to four carbon atoms and includes methoxy, ethoxy, propoxy, butoxy, hexoxy, 1-methylethoxy and 1,1-dimethylethoxy. The latter radical is known commonly as tertiary-butyloxy.

With further reference to the substrates and assays of this invention, HCMV protease is an endoproteolytic enzyme which cleaves its precursor protein at multiple different sites (Maturation, Release, & Internal) having the general consensus V-(N/E/K)-A↓(S/A)(Gibson, W. et al., vide infra). Efficient hydrolysis by HCMV protease of peptide substrates corresponding to the natural cleavage sites generally requires the minimum $P_4$ to $P'_4$ amino acid sequence. Moreover the enzyme cleaves maturation site peptides up to 30-fold more efficiently than those corresponding to the release site.(The maturation sequence was therefore chosen as the starting point for both the synthesis of substrates and the development of peptide-based inhibitors.)

Our initial fluorogenic substrate having the structure of Formula 1:

ABz-Val-Val-Asn-Ala-Ser-Ser-Arg-Leu-Tyr(3-NQ$_2$)Arg-OH (1)
[SEQ ID NO: 2]

used the anthranilamide/nitrotyrosine system. This choice considered both the excellent spectral overlap properties of this donor/acceptor pair and the ease of synthesis by solid-phase chemistry {Mendal, M. et al., vide infra and Gron, H., Mendal, M., Breddam. K. (1992), *Biochemistry* 31, 6011–6018}. The substrate of formula 1 encompassed the sequence $P_4$-$P'_4$ of the maturation site in which the $P'_2$ cysteine residue was replaced by serine to prevent oxidation problems. The anthranilamide moiety conveniently capped the N-terminus end whereas 3-nitrotyrosine was positioned eight residues away, preceding the C-terminal arginine residue which was incorporated to increase solubility. The relatively short distance between the donor/acceptor pair and the nature of the amino acid sequence permitted efficient internal fluorescence quenching. Indeed the ratio $F_0/F_\infty$ was ≈4% upon excitation at 312 nm and emission at 415 nm ($F_0$ & $F_\infty$ are the fluorescence measured for the substrate and the N-terminal hydrolysis product respectively at equal concentrations). In addition, no substantial intermolecular quenching of the fluorescence by excess substrate interfered with the signal below 15 $\mu$M (inner filter effect), consistent with earlier reports for this class of substrates (Mendal, M. et al., vide infra). Above this concentration significant inner filter effect became apparent.

The kinetic parameters $k_{cat}$ & $K_m$ for the substrate of formula 1 in presence of 0.5 M Na$_2$SO$_4$ using 50 nM HCMV protease were 0.20 s$^{-1}$ and 760 $\mu$M respectively as measured by HPLC (Table II).

TABLE II

KINETIC PARAMETERS OF HCMV PROTEASE SUBSTRATES

| Substrate | $k_{cat}$ (s$^{-1}$) | $K_M$ ($\mu$M) | $k_{cat}/K_M$ (M$^{-1}$s$^{-1}$) |
|---|---|---|---|
| 1[a,c] | 0.20 | 760 | 260 |
| 2[a,d] | 0.051 | 3.2 | 15940 |
| 3[a,d] | 0.035 | 13.2 | 2650 |
| 4[b,c] | 0.086 | 422 | 205 |
| 5[b,c] | 0.045 | 19 | 2370 |

[a]Using 50 nM HCMV protease (total monomer concentration).
[b]Using 200–500 nM HCMV protease.
[c]Determined by HPLC.
[d]Determined by fluorometry.

The resulting specificity constant $k_{cat}/K_m$ of 260 M-1$_s$-1 compares favorably with other maturation site substrates (Gibson, W. et al., vide supra). However, the limited solubility of the substrate of formula 1 and its high $K_m$ value limited the accuracy of the individual parameters and did not permit determinations of the kinetic parameters by fluorescence due to the inner filter effect. Nevertheless, below this concentration the substrate can conveniently monitor HCMV protease activity.

The substrate of formula 1 was used to implement a 100 nM HCMV protease assay for routine screening of inhibitors. However rapid progress in the structure-activity relationship (SAR) studies eventually required a reduction of the enzyme concentration in order to differentiate between potent compounds. Indeed an IC$_{50}$ value cannot be lower than half the enzyme concentration in the assay. Reducing the enzyme therefore permits accurate determination of the potency of active inhibitors.

It was found that the direct introduction of Tbg-Tbg-Asn (Me)$_2$ in place of the natural $P_4$-$P_2$ Val-Val-Asn sequence into the substrate of formula 1 gave a more efficiently cleaved fluorogenic substrate having the structure of formula 2:

ABz-Tbg-Tbg-Asn(Me)$_2$-Ala-Ser-Ser-Arg-Leu-Tyr(3-NO2)-Arg-OH (2) [SEQ ID NO: 3]

The fluorescent properties of the substrate of formula 2 were similar to those of the substrate of formula 1 but its kinetic features were significantly improved. The kinetic parameters $k_{cat}$ & $K_m$ for the substrate of formula 2 in the standard conditions were 0.051 s$^{-1}$ and 3.2 $\mu$M respectively as measured by fluorometry (Table II). The resulting specificity constant $k_{cat}/K_m$ of 15940 M$^{-1}$s$^{-1}$ was 60-fold greater than for the unoptimized substrate. The large reduction in $K_m$ was responsible for this substantial increase in activity and reflected the anticipated improvement in binding. The inhibitory activity of the N-terminal product ABz-Tbg-Tbg-Asn(Me)$_2$-Ala-OH was determined to establish if it could interfere with the course of the reaction. An IC$_{50}$ value above 75 $\mu$M clearly indicated that its influence could not be felt significantly in the substrate concentration range used.

These improved kinetic parameters conferred to the substrate of formula 2 a number of significant advantages over other existing fluorogenic substrates. First, the substrate readily permitted the development of an assay utilizing only 5 nM HCMV protease thus allowing low nanomolar potency inhibitors to be unequivocally characterized. Secondly, substrate concentrations significantly above the $K_m$ value but below the limit imposed by the inner filter effect were accessible for continuous fluorescence monitoring thus allowing a variety of kinetic analysis to be rigorously performed simply and rapidly. To date only tedious and time-consuming HPLC protocols could be used for certain applications as none of the available well characterized HCMV protease fluorogenic substrates displayed fluorescence properties compatible with measurements above $K_m$ {Margosiak, S. A., Vanderpool, D. L., Sisson, W., Pinko, C., Kan, C.-C. (1996) *Biiochemistry* 35, 5300–5307}. Such measurements are essential for accurate determination of individual $k_{cat}$ & $K_m$ values and for analysis of modes of inhibition.

Figure 1:
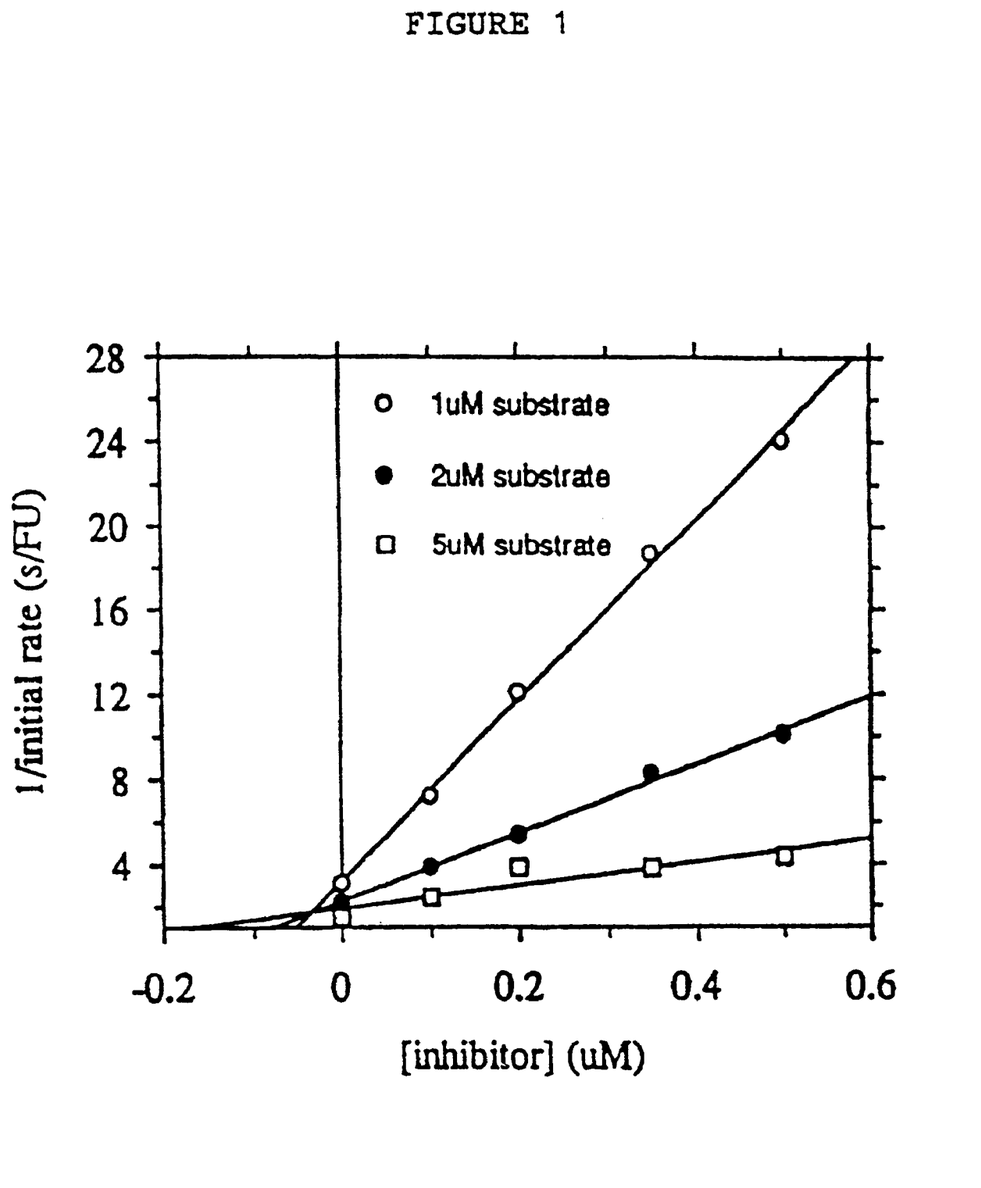
FIG. 1 illustrates the inhibitory effect of a peptide inhibitor on HCMV protease at various concentrations of an improved substrate of this application.

For example the mode of inhibition of the HCMV N$_o$ protease peptide-based ketoamide inhibitor DATbg-Tbg-Asn(Me$_2$)-Ala-CONHCH$_2$Ph [SEQ ID NO:4J was shown to be competitive by Dixon-plot analysis of the initial rate of hydrolysis at different substrate 2 and inhibitor concentrations (FIG. 1). The convenient use of fluorescence in this experiment was possible since a range of substrate concentrations from 0.4 to 2.5 $K_m$ was permitted. Substrate 1 could not be used in this application since its $K_m$ value is well above the inner filter limit.

The aforementioned ketoamide inhibitor was prepared by the procedure of example 9.

The most important factors limiting the use of these internally quenched fluorogenic substrates are the presence of the inner filter effect around 15–20 $\mu$M and significant fluorescence background at low concentrations. In an attempt to further improve our arsenal of fluorogenic substrates, we decided to introduce the fluorescent group 7-amino-4-methylcoumarin (AMC) at the scissile bond {Zimmerman, M., Yurewicz, E., Patel, G. (1976) Anal. Biochem. 70, 258–262}. AMC has been successfully used in a variety of fluorescent serine and cysteine protease substrates {Proteolytic Enzymes: Serine and Cysteine Peptidases (1994) in Meth. Enzymol. 244, (Barrett, A. J., Ed.), pp.1–765}. Its main advantage relies on a high signal to noise ratio as fluorescence appears only upon cleavage and does not require any other accessory group. Addition of this fluorophore directly on the $P_1$ alanine residue resulted in substitution of the P' residues by the AMC moiety. Although these residues are essential in natural peptide substrates, we reasoned that the optimized Tbg-Tbg-Asn(Me)$_2$ $P_4$-$P_2$ sequence may amply compensate for their replacement by the AMC group. The substrate having the formula 3:

N-Ac-Tbg-Tbg-Asn(Me)$_2$-Ala-AMC (3) [SEQ ID NO: 5]

was synthesized as a representative member of a new family of short fluorogenic HCMV protease substrates. The substrate of formula 3 displayed excellent kinetic properties with $k_{cat}$ & $K_m$ values in the assay conditions of 0.035 s$^{-1}$ and 13.2 $\mu$M respectively as measured by fluorometry (Table II). The resulting specificity constant, $k_{cat}/K_m$, of 2650 M$^{-1}$s$^{-1}$ was 10-fold greater than for the substrate of formula 1 despite lacking four P' residues and only 6-fold smaller than the substrate of formula 2. The substrate of formula 3 represents the first demonstration that HCMV protease (and probably all other herpesvirus proteases) does not absolutely require the presence of P' amino acids for efficient cleavage. The intense fluorescence signal generated by the release of the AMC group combined to a negligible background confer to the substrate of formula 3 the advantages of facile cleavage detection on low sensitivity instruments and accessibility to a large range of concentrations within the solubility limitations (Knight, G. C. et al., vide infra).

More specifically, in accordance with the present invention, improved substrates of formula I and assays for herpesvirus protease utilizing the improved substrates are disclosed. The assays can be used to measure the activity of CMV protease, by contacting the herpes virus protease with the improved substrate and monitoring the cleavage of the substrate.

A preferred class of the substrates is represented by formula I wherein Z is an aromatic amino radical or phenoxy radical derived from 7-amino-4-methylcoumarin, 6-amino-1-naphthalenesulfonamide, rhodamine 110, 2-naphthylamine, 4-methoxy-2-naphthylamine, 4-nitroaniline or 4-nitrophenol.

Another preferred class of substrates includes substrates of formula I wherein the substrate is covalently linked to a fluorescent donor radical and a fluorescent acceptor radical, the donor and acceptor radicals being separated by the alanine residue and 7 to 12 additional amino acid residues.

Still another preferred group of substrates is represented by formula I wherein the donor/acceptor radical pair is selected from the following pairs:
EDANS/DABCYL,
tryptophan/2,4-dinitrophenyl,
tryptophan/DANSYL,
7-methoxycoumarin/2,4-dinitrophenyl,
2-aminobenzoyl/2,4-dinitrophenyl or
2-aminobenzoyl/3-nitrotyrosine.

Other useful substrates of this invention are those linked to a detectable label and an affinity tag. Practical and useful detectable labels are radioactive labels such as $^{125}$I, or β-galactosidase, para-nitrophenol or para-nitroaniline. Practical and useful affinity tags are those derived from biotin (or derivatives thereof), polyhistidine, an amylose sugar moiety or a defined epitope recognizable by a specific antibody. Such labels and affinity tags are attached to the substrate by well known methods.

A method of measuring the activity of a herpes protease, as well as a method of identifying an inhibitor of a herpes virus protease, are described in more detail and exemplified hereinafter.

The following examples illustrate further this invention.

In connection with the examples please note the following:

All natural amino acid derivatives and the N-α-Fmoc-N$^G$-Pmc-L-Arginine-Wang resin were purchased from Bachem (Torrance, Calif., USA). 3-Nitro-L-tyrosine was purchased from Sigma Chemical Co., St. Louis, Mo., USA, and 2-aminobenzoic acid (ABz) and 7-amino-4-methylcoumarin (AMC) were purchased from Aldrich Chemical Co., Milwaukee, Wis., USA and the compounds were protected by standard methods. Peptide substrate 1 was prepared on an Advanced Chemtech peptide synthesizer model ACT396/5000 MPS. Substrate 2 was prepared using a shaker-type peptide synthesizer Coupler® 250C from Vega Biotechnologies (Dupont Co., Wilmington, Del., USA). $^1$H NMR spectra were recorded on a Bruker 400 MHz spectrometer; the chemical shifts (δ) are reported in parts per million. Analytical HPLC's were performed on a Waters instrument equipped with a Vydac C18 reversed-phase column, 0.46×25 cm, 5 $\mu$m, 300 Å (gradient: 5 to 65% acetonitrile/water containing 0.06% TFA in 25 min at a flow rate of 1.5 mL/min). Amino acid analysis were performed by the PICO-TAG® method using a Waters HPLC system. For enzyme kinetics, HPLC determinations were made using Perkin-Elmer Xpress 3X3CR C8 reversed-phase cartridge columns. Fluorescence measurements were performed in quartz cuvettes on a Perkin-Elmer LS50B luminescence spectrophotometer.

Abbreviations or symbols used in the examples, or throughout the present specification, include Aba, 2-aminobutyric acid; ABz, 2-aminobenzoic acid or anthranilic acid; Ac, acetyl; AMC, 7-amino-4-methylcoumarin; Asn(Me)$_2$, 2(S)-amino-4-(dimethylamino)-4-oxobutanoic acid; Boc, tertiary butyloxycarbonyl; DABCYL, 4-{{4-(dimethylamino)phenyl}azo}benzoic acid; DANSYL, 5-(dimethylamino)naphthalene-1-sulfonyl; DATbg, desamino-tertiary-butylglycine (3,3-dimethylbutylbutanoic acid); DCC: N,N'-dicyclohexylcarbodiimide; DIC, 2-dimethylaminoisopropyl chloride hydrochloride; DIPEA, disopropylethylamine; DMF, N,N,-dimethylformamide; DMSO, dimethylsulfoxide; DTT, dithiothreitol; EDANS, 5-{(2-aminoethyl)-amino}naphthalene-1-sulfonic acid; Et$_2$O, diethyl ether; EtOAc, ethyl acetate; Fmoc, 9-fluorenylmethyloxycarbonyl; HCMV, human cytomegalovirus; HOBT, 1-hydroxybenzotriazole hydrate; IPTG, isopropyl-β-D-thiogalactopyranoside; MeOH, methanol; MES, 4-morpholineethanesulfonic acid; NMP, N-methylpyrrolidone; PCR, polymerase chain reaction; Ph, phenyl; Pmc, 2,2,5,7,8 - pentamethylchroman-6-sulfonyl; PMSF, phenylmethylsulfonyl fluoride; QSAR, quantitative structure activity relationship; Tbg, tertiary-butylglycine; tBu, tertiary-butyl; TFA, trifluoroacetic acid; Trt, triphenylmethyl; TBTU, O-(benzotriazol-1-yl)-1,1,3,3-tetramethyluronium tetrafluoroborate; TCEP, tris(2-carboxyethyl)phosphine hydrochloride; TRIS, tris(hydroxymethyl)aminomethane; Tyr(3-NO$_2$),3-nitrotyrosine.

The substrate positions are denoted P$_i$, ... ,P$_2$, P$_1$↓P'$_1$, P'$_2$, ... , P'$_j$, wherein cleavage takes place at the arrow {Schechter, J., Berger, A.(1970) *Philos. Trans. R. Soc. London*, Ser.B. 257, 249–264}.

EXAMPLE 1

Preparation of recombinant wild-type HCMV protease PCR amplified HCMV protease gene from genomic DNA (UL80 gene from HCMV strain AD169, aa 1-256) was cloned in the NdeI/BamHI restriction sites of the plasmid vector pET-17b and expressed in *Escherichia Coli* strain BL21(DE3)pLYSs. Following expression by induction with IPTG, cells were harvested and resuspended in lysis buffer (50 mM Tris/HCl pH 8.0, 1 mM EDTA, 1 mM DTT, 25 mM NaCl, and 1 mM PMSF) and sonicated for complete lysis and DNA breakage. Protease inclusion bodies were harvested by centrifugation. The harvested material was washed twice in lysis buffer containing 0.1% nonaethylene glycol octylphenyl ether (NP-40, Sigma Chemical Co.). Solubilization and denaturation of the harvested material were performed by resuspending the inclusion bodies in 100 mM Tris/HCl pH 8.0, 1 mM EDTA, 100 mM DTT, 50 mM NaCl, and 7 M urea and incubating at 37° C. for 2 h. After centrifugation to eliminate insoluble matter, the supernatant was extensively dialyzed in 50 mM MES pH 5.0, 0.1 mM EDTA, 10 mM DTT, and 7 M urea for cation exchange chromatography on Resource S column. The resulting pool of protease-containing fractions was then dialyzed in 25 mM Tris/HCl pH 7.8, 1 mM EDTA, and 1 M urea and diluted to ≈100 μg/ml to which 0.2 mM oxidized glutathione and 2 mM reduced glutathione were added. Incubation was performed overnight at 4° C. with gentle shaking and renaturation was then completed by extensive dialysis in 25 mM Tris/HCl pH 7.8, 1 mM EDTA, 1 mM DTT, and 100 mM NaCl followed by dialysis in storing buffer (20 mM acetate pH 5.0, 0.1 mM EDTA, 1 mM DTT, and 50 mM NaCl) before concentration of the sample to give the desired protease.

EXAMPLE 2

ABz-Val-Val-Asn-Ala-Ser-Ser-Arg-Leu-Tyr(3-NO$_2$)-Arg-OH (1) [SEQ ID NO: 2]

The peptide 1 was assembled on N-a-Fmoc-N$^G$-Pmc-L-Arginine Wang resin (0.31 mmol/g, 0.2 mmol, 650 mg) using a Fmoc/DCC/HOBt solid-phase procedure on a ACT396 MPS peptide synthesizer. Side chain protecting groups were Pmc for Arg, Trt for Asn, and O-tBu for Ser. The Fmoc amino protecting groups were removed at every stage by washing the resin with NMP, shaking with a solution of 25% piperidine in NMP (3.5 mL for 5 min then 3.5 mL for 20 min) and washing successively with NMP, MeOH and NMP. The amino acids were coupled as their activated HOBt esters, utilizing four equivalents of the reagents as follows: A 0.5 M solution of the Fmoc-protected amino acid and of HOBt in NMP (1.6 mL, 0.8 mmol of each) was added automatically to the deprotected resin, followed by addition of a 0.5 M DIC solution in NMP (1.6 mL, 0.8 mmol). The reaction vessel was shaken for 4 h. The solution was then removed by filtration and the remaining resin was washed twice with 3.5 mL of NMP. Fresh portions of reagent solutions were added and the coupling was repeated for 4 h. At the completion of each cycle, the resin was washed successively with NMP, MeOH and NMP. The last coupling with N-Boc-2-aminobenzoic acid (Boc-ABz-OH) was performed with only 1.1 equivalent of the reagents for 4 h (single coupling) in order to avoid formation of the tyrosine esterification by-product (the tyrosine hydroxyl is unprotected). The resulting resin was washed successively as above, followed by additional washings with CH$_2$Cl$_2$, and then dried under reduced pressure. Complete deprotection and cleavage of the resin was achieved by stirring the resin (890 mg) with 10 mL of a mixture TFA/anisole/thioanisole/ethanedithiol (90/2/3/5) for 2.5 h at room temperature under a nitrogen atmosphere. The mixture was suction-filtered into Et$_2$O (200 mL) to give a yellow precipitate. This suspension was cooled in an ice-bath and filtered through a 45 μm membrane to give a yellow solid (281 mg, 47% homogeneity by analytical HPLC). The crude product was purified in two batches (2×140 mg) by preparative HPLC (Whatman HPLC column, 22.0 mm×500 mm, Partisil® 10 ODS-3 M/20-50, particle size 10 μm, solvents: A=0.06% TFA/H$_2$O, B=75% CH$_3$CN-25% H$_2$O containing 0.06% TFA; gradient 0 to 35% B in 60 min). Following lyophilization, compound 1 was recovered as an amorphous yellow solid (101.5 mg , 95% HPLC homogeneity). This material was repurified on the same preparatory HPLC using a faster gradient 0 to 40% B in 60 min. The product (62 mg, 96% HPLC homogeneity) was purified a third time by preparative HPLC using an even faster solvent gradient (0 to 50% B in 60 min) to yield 31 mg (99% HPLC homogeneity)of the desired peptide of formula 1. MS-FAB (thioglycerol): MH+=1329.0 Da. Amino acid analysis: calc.(obs.) Asx 1 (0.99), Ser 2 (1.93), Arg 2 (1.99), Ala 1 (1.01), Leu 1 (1.07), Val 2 (1.48, partial hydrolysis), Tyr(3-NO$_2$) 1 (present), 2-aminobenzoic acid 1 (present), Peptide recovery: 79%±6%.

EXAMPLE 3

ABz-Tbg-Tbg-Asn(Me)$_2$-Ala-Ser-Ser-Arg-Leu-Tyr(3-NO$_2$)-Arg-OH (2) [SEQ ID NO: 3]

This peptide was essentially synthesized as described above using a shaker-type peptide synthesizer "Vega Biotechnologies Coupler® 250 C". A mixture of Fmoc-L-amino acid (1 mmol), HOBt (140 mg, 1 mmol) and 1M solution of DCC in CH$_2$Cl$_2$ (1 mL, 1 mmol), NMP (2 mL) and CH$_2$Cl$_2$ (6 mL) was stirred at room temperature (20–22° C.) for 30 min. The resulting suspension was filtered. The filtrate was diluted with NMP (10 mL) and added to the Fmoc-deprotected resin. Complete coupling was ensured by Kaiser tests performed on a resin sample. After the final coupling the peptide-resin was washed as described above and dried under reduced pressure. The residue was stirred with 10 mL of a mixture TFA/anisole/ thioanisole/ethanedithiol (90/2/3/5) for 4 h under nitrogen. The resulting mixture was poured into cold Et$_2$O (200 mL) to give a yellow precipitate. After filtration, a yellow solid was recovered (450 mg, HPLC indicated the presence of two main components: 24%, 19.28 min. and 34%, 21.88 min). The crude product (200 mg) was purified by a preparative HPLC (Whatman HPLC column, 22.0 mm×500 mm, Partisil® 10 ODS-3 M/20-50, particle size 10 μm, solvents: A=0.06% TFA/H$_2$O, B=75% CH$_3$CN-25% H$_2$O containing 0.06% TFA; gradient: 10 to 40% B in 30 min, then 40% to 50% B in 30 min). Following lyophilization, a yellow compound of formula 2 was obtained as an amorphous solid (24 mg, >99% HPLC homogeneity). MS-FAB (thioglycerol): MH+=1384.9 Da, Amino acid analysis : calc.(obs.) Asx 1 (1.03), Ser 2 (1.86), Arg 2 (2.02), Ala 1 (1.05), Leu 1 (1.05), Tbg 2 (1.12, partial hydrolysis), Tyr(3-NO$_2$) 1 (0.88), 2-aminobenzoic acid 1 (0.71), Peptide recovery: 75.2%±0.6%.

EXAMPLE 4

N-Acetyl-Tbg-Tbg-Asn(Me)$_2$-Ala-AMC (3) [SEQ ID NO: 5]

This substrate was synthesized in solution using the following procedure:

(a) Boc-Ala-AMC (4). N,N-diisopropylethyl amine (DIPEA, 3.6 mL 20.5 mmol) was added to an ice-cold solution of Boc-L-alanine (1.55 g, 8.20 mmol), 7-amino-4-methylcoumarin (MCA, 0.72 g, 4.1 mmol) and TBTU (2.63 g, 8.19 mmol) in DMF (10 mL). The mixture was stirred in an ice bath for 30 min under nitrogen, then at room temperature in the dark for 15 h. The reaction mixture was diluted with EtOAc (60 mL) and the solution was washed successively with 2N NaOH (3×30 mL), 1N HCl (3×30 mL), water (3×20 mL) and saturated brine (2×20 mL). The organic solution was then dried (Na$_2$SO$_4$), filtered and concentrated under reduced pressure to give a white solid in residual EtOAc. This residue was triturated with Et$_2$O (50 mL), filtered and rinsed successively with Et$_2$O (3×20 mL) and hexane (3×20 mL) and was dried under reduced pressure to give a white solid product (0.657 g, 46% yield, 98% HPLC homogeneity). MS-FAB: MH$^+$=347 Da; $^1$H NMR (400 MHz, DMSO-d6) δ10.36 (s, 1 H), 7.76 (d, J=1.6 Hz, 1H), 7.72 (d, J=8.6 Hz, 1H), 7.50 (d, J=8.6 Hz, 1H), 7.16 (d, J=6.7 Hz, 1 H), 6.25 (s, 1H), 4.13 (m, J=7.0 Hz, 1H), 2.40 (s, 3H),1.38 (s, 9H), 1.28 (d, J=6.7 Hz, 3H). (b) HCl * H-Ala-AMC (5). Boc-Ala-AMC (4) (0.557 g, 1.61 mmol) was dissolved in 4N HCl/dioxane solution (30 mL). After 5 min of stirring a white precipitate began to form. The mixture was stirred at room temperature for 45 min. under a nitrogen atmosphere in the dark and then concentrated under reduced pressure to semi-dryness. The residual white paste was triturated with Et$_2$O (50 mL), filtered and dried under reduced pressure to give compound 5 as an off-white, yellowish solid (0.495 g, quantitative yield, 96% HPLC homogeneity). This product was not characterized further and used directly in the next synthetic step.

(c) 13oc-Asn(Me)$_2$-Ala-AMC (6). N,N-diisopropylethyl amine (DIPEA, 1.7 mL, 9.76 mmol) was added to a solution containing N',N'-dimethyl-Boc-L-Asparagine (0.5 g, 1.92 mmol), crude 5 (assumed 1.61 mmol) and TBTU (0.617 g, 1.92 mmol) in DMF (5 mL). The mixture was stirred under nitrogen at room temperature in the dark for 2.5 h. The reaction mixture was then diluted with EtOAc (50 mL) and the solution was washed successively with 2N NaOH (3×20 mL), 1N HCl (3×20 mL), water (2×20 mL) and saturated brine (2×20 mL). During the washings the product began to precipitate; it was redissolved by the addition of more EtOAc (30 mL). The organic solution was then dried (Na$_2$SO$_4$), filtered and concentrated under reduced pressure to give a semi-solid, white residue. This residue was triturated with Et$_2$O (100 mL) and filtered through a 45 μm membrane. The resulting solid was rinsed successively with Et$_2$O (3×20 mL) and hexane (3×20 mL). Thereafter, it was dried under reduced pressure to give a white, solid product (0.470 g, 60% yield, 99% HPLC homogeneity). MS-FAB: MH$^+$=489 Da, (M+Na$^+$) =511 Da, $^1$H NMR (400 MHz, DMSO-d6) δ10.08 (s, 1H), 8.27 (d, J=7.0 Hz, 1H), 7.82 (d, J=1.9 Hz, 1H), 7.73 (d, J=8.6 Hz, 1H), 7.61 (dd, J=8.6, 1.9 Hz, 1H), 6.96 (d, J=7.6 Hz, 1H), 6.26 (d, J=1.3 Hz, 1H), 4.39 (m, 1H), 4.34 (m, 1H), 2.96 (s, 3H), 2.85 (s, 3H), 2.72 (d, J=6.4 Hz, 2H), 2.40 (d, J=0.9 Hz, 3H), 1.39 (s, 9H), 1.34 (d, J=7 Hz, 3H). (d) HCl H-Asn(Me)$_2$-Ala-AMC (7). Boc-Asn (Me$_2$)-Ala-AMC (6) (0.370 g, 0.76 mmol) was deprotected in 2 h using the standard procedure described for 5 resulting in recovery of compound 7 (0.320 g, 100 % yield, 99% HPLC homogeneity). This product was not characterized further but was used directly as such for the next step.

(e) Boc-Tbg-Asn(Me)$_2$-Ala-AMC (8). N,N-diisopropylethylamine (DIPEA, 0.8 mL, 4.59 mmol) was added to a solution containing Boc-L-tert-butyl-glycine (Boc-Tbg-OH, 0.21 g, 0.9 mmol), crude 7 (assumed 0.76 mmol) and TBTU (0.29 g, 0.9 mmol) in DMF (3.5 mL). Treatment of the mixture in the same manner as described for the corresponding mixture in the above preparation of compound 6 gave a white, solid product (0.358 g, 79% yield, 99% HPLC homogeneity). MS-FAB: MH$^+$=602 Da, $^1$H NMR (400 MHz, DMSO-d6) δ9.96 (s, 1H), 8.38 (d, J=7.3 Hz, 1H), 8.15 (d, J=7.3 Hz, 1H), 7.86 (d, J=1.9 Hz, 1H), 7.74 (part of a AB system, d, J=8.6 Hz, 1H), 7.68 (part of a AB system, dd, J=8.6, 1.9 Hz, 1H), 6.53 (d, J=8.9 Hz, 1H), 6.27 (s, 1H), 4.66 (m, 1H), 4.38 (quintet, J=7.3 Hz, 1H), 3.87 (d, J=9.2 Hz, 1H), 2.98 (s, 3H), 2.86 (s, 3H), 2.85-2.70 (m, 2H), 2.40 (s, 3H), 1.39 (s, 9H), 1.33 (d, J=7.3 Hz, 3H), 0.89 (s, 9H).

(f) HCl . H-Tbg-Asn(Me)$_2$-Ala-AMC (9). Boc-Tbg-Asn (Me)$_2$-Ala-AMC (8) was deprotected in 3h using the standard procedure described for 5. In this manner, compound 9 was obtained (0.240 g, quantitative yield, 97% HPLC homogeneity). This product was not characterized further but was used as such for the next step.

(g) Boc-Tbg-Tbg-Asn(Me)$_2$-Ala-AMC (10). N,N-diisopropylethyl amine (DIPEA, 0.5 mL, 2.57 mmol) was added to a solution containing Boc-L-tertiary-butyl-glycine (Boc-Tbg-OH, 0.119 g, 0.515 mmol), crude 9 (assumed 0.43 mmol) and TBTU (0.165 g, 0.515 mmol) in DMF (2 mL). The mixture was treated in the same manner as described for the corresponding mixture in the preparation of compound 6. In this manner, a white solid was obtained (0.227 g, 74% yield, 96% HPLC homogeneity). MS-FAB: MH$^+$=715 Da, $^1$H NMR (400 MHz, DMSO-d6) δ9.95 (s, 1H), 8.35 (d, J=7.6 Hz, 1H), 8.32 (d, J=7.6 Hz, 1H), 7.86 (d, J=1.9 Hz, 1H), 7.74 (part of a AB system, d, J=8.6 Hz, 1H), 7.68 (part of a AB system, dd, J=8.6 Hz, 1.9 Hz, 1H), 7.53 (d, J=9.2 Hz, 1H), 6.85 (d, J=9.2 Hz, 1H), 6.27 (d, J=0.9 Hz, 1H), 4.64 (m, 1H), 4.39 (quintet, J=7.3 Hz, 1H), 4.29 (d, J=8.9 Hz, 1H), 3.93 (d, J=9.5 Hz, 1H), 2.97 (s, 3H), 2.86 (s, 3.5H), 2.82 (part of a AB system, d, J=8.9 Hz, 0.5H), 2.67 (part of a AB system, dd, J=16.2, 5.1 Hz, 1H), 2.40 (d, J=0.9 Hz, 3H), 1.39 (s, 9H), 1.32 (d, J=7.3 Hz, 3H), 0.911 (s, 9H), 0.907 (s, 9H).

(h) HCl H-Tbg-Tbg-Asn (Me)$_2$-Ala-AMC (11). Boc-Tbg-Tbg-Asn(Me)$_2$-Ala-AMC (10) (0.127 g, 0.177 mmol) was deprotected in 2 h using the standard procedure described for compound 5. Hence, compound 11 was obtained (0.125 g, quantitative yield, 96% HPLC homogeneity). This product was not characterized further but was used directly in the next step. (i) Ac-Tbg-Tbg-Asn (Me)$_2$-Ala-AMC (3). Acetic anhydride (50 mL, 0.53 mmol) was added to a solution of crude 11 (assumed 0.177 mmol) in pyridine (1 mL). The mixture was stirred at room temperature in the dark and under a nitrogen atmosphere for 1 h. The reaction mixture was then diluted with EtOAc (30 mL). The solution was washed successively with 1N HCl (3×20 mL), water (3×20 mL), saturated brine (2×20 mL), dried with Na$_2$SO$_4$, filtered and concentrated under reduced pressure. The semi-solid residue was triturated with Et$_2$O (100 mL) and filtered through a 45 μm membrane. The resulting solid was rinsed successively with Et$_2$O (3×10 mL) and hexane (3×10 mL) and dried under reduced pressure for 18 h to give substrate 3 as a white, solid product (90 mg, 77% yield, 98% HPLC homogeneity). MS-FAB: M$^{H+}$=657 Da, $^1$H NMR (400 MHz, DMSO-d6) δ9.95 (s, 1H), 8.39 (d, J=7.3 Hz, 1H), 8.20 (d, J=7.3 Hz, 1H), 7.86 (d, J=1.9 Hz, 1H), 7.82 (d, J=9.2 Hz, 1H), 7.73 (part of a AB system, d, J=8.6 Hz, 1H), 7.67 (part of a AB system, dd, J=8.6, 1.9 Hz, 1H), 7.61 (d, J=8.9 Hz, 1H), 6.26 (d, J=1.3 Hz, 1H), 4.62 (m, 1H), 4.37 (m, 1H), 4.35 (d, J=9.6 Hz, 1H), 4.22 (d, J=8.9 Hz, 1H), 2.97 (s, 3 H), 2.86 (s, 3H), 2.81 (part of a AB system, dd, J=16.2, 8.6 Hz, 1H), 2.70 (part of a AB system, d, J=16.2, 4.1 Hz, 1H), 2.40 (d, J=1.3 Hz, 3H), 1.89 (s, 3H), 1.32 (d, J=7.3 Hz, 3H), 0.907 (s, 9H), 0.904 (s, 9H). Amino acid analysis: calc.(obs.) Asx 1 (0.99), Ala 1 (1.01), Tbg 2 (1.15, partial hydrolysis), 7-amino-4-methylcoumarin 1 ( 1 ).

EXAMPLE 5 d-Biotin-Arg-Gly-Val-Val-Asn-Ala-Ser-Ser-Arg-Leu-Ala-Tyr-NH$_2$ (12) [SEQ ID NO: 6]

This compound was synthesized by using an Applied Biosystem peptide synthesizer (model 430 A) and following a Fmoc/DCC/HOBt protocol. The synthesis was done on 0.25 mmol of Rink resin (Advanced Chemtech, Louisville Ky., USA) with 1 mmol of protected amino acids and the coupling was allowed to proceed 1 h. Single coupling was employed for Tyr, Ala, Leu and Arg while double coupling was employed for Ser, Ser, Ala, Asn, Val, Gly and Arg. The biotin was coupled with TBTU in a 1:3 mixture of DMSO/NMP for 24 h. After the final coupling the peptide-resin was washed as described above and dried under reduced pressure. The cleavage and concomitant side chain deprotection was performed in 10 mL of a mixture of TFA/phenol/thioanisole/ ethanedithiol/H$_2$O (90/3.5/2.5/1.2/2.5) for 2.5 h under a nitrogen atmosphere. The cleavage cocktail was concentrated under reduced pressure. The residue was diluted with 20 mL of Et$_2$O. The resulting precipitate was collected on a filter and purified by reversed phase semi-preparative HPLC (Whatman HPLC column, 22.0 mm×500 mm, Partisil® 10 ODS-3 M/20-50, particle size 10 μm, solvents: A=0.06 % TFA/H$_2$O, B=75% CH$_3$CN-25% H$_2$O containing 0.06% TFA; gradient: 0 to 40% B in 60 min). The fractions containing the desired product were combined, lyophilized and repurified under the same conditions to afford, after lyophilization, the desired compound as a white amorphous solid (88 mg, 96% HPLC homogeneity). MS-FAB (thioglycerol) : MH$^+$=1517.6 Da, Amino acid analysis : calc.(obs.) Asx 1 (0.97), Ser 2 (1.79), Gly 1 (1.03), Arg 2 (1.87), Ala 2 (2.06), Tyr 1 (0.98), Val 2 (1.23, partial hydrolysis), Leu 1 (1.09), Peptide recovery: 68% ±1%.

EXAMPLE 6 d-Biotin-Arg-Gly-Tbg-Tbg-Asn (Me) $_2$-Ala-Ser-Ser-Arg-Leu-Ala-Tyr-NH$_2$ (13) (SEQ ID NO: 7]

This compound was prepared on a ACT396 MPS peptide synthesizer using four equivalents of amino acid, HOBt hydrate and TBTU and eight equivalents of DIPEA. Each amino acid was double coupled. The reaction time for each coupling was 1 h. At the end of the synthesis, the biotin residue was incorporated using a similar protocol as the one described above. The cleavage and concomitant side chain deprotection was performed in 10 mL of a mixture of TFA/anisole/thioanisole/ethanedithiol (90/3/5/2) for 2.5 h under a nitrogen atmosphere. The cleavage cocktail was concentrated under reduced pressure. The residue, was diluted with 20 mL of Et$_2$O. The resulting precipitate formed was filtered and purified by reversed phase semi-preparative HPLC (Waters PrepPak 500 cartridge, 60 mm×330 mm, C18, particle size 15 μm, solvents: A=0.05M NH$_4$OAc/H$_2$O, B=CH$_3$CN; gradient: 0 to 35% B in 80 min.; flow rate: 50 mL/min.). The fractions containing the product were combined, lyophilized and repurified (Waters PrepPak 500 cartridge, 60 mm×330 mm, C18, particle size 15 μm, solvents: solvents: A=0.06% TFA/H$_2$O, B=75% CH$_3$CN-25% H$_2$O containing 0.06% TFA; gradient: 0 to 40% B in 90 min. flow rate: 50 mL/min.). After lyophilization, the desired compound was isolated as a white amorphous solid (60 mg, 95% HPLC homogeneity). MS-FAB (thioglycerol): MH$^+$= 1573.8 Da, Amino acid analysis : calc.(obs.) Asx 1 (1.02), Ser 2 (1.84), Arg 2 (2.01), Ala 2 (2.05), Tyr 1 (1.00), Leu 1 (1.05), Tbg 2 (0.25, partial hydrolysis), Peptide recovery: 66% ±2%.

$^{125}$I labeling (13a)

$^{125,}$ labeling of Biotin-Arg-Gly-Tbg-Tbg-Asn(NMe)$_2$-Ala-Ser-Ser-Arg-Leu-Ala-Tyr-NH$_2$ (13)

Substrate 13 was labeled with Na $^{125}$I using the insoluble iodination reagent 1,3,4,6-tetrachloro-3α, 6α-diphenylglycouril (IODO-GEN® from Pierce) as instructed by the manufacturer. Shortly, 250 μL of a 100 μg/mL solution of IODO-GEN® in chloroform was slowly evaporated with a nitrogen stream in a 16×100 mm borosilicate tube. To the tube was added 187μL ice-cold potassium phosphate buffer 0.5M pH 7 and 13 μL substrate 13 1 mM in DMSO. Iodination was initiated by addition of 10 L Na$^{125}$I 1 mCi. The reaction was allowed to proceed for 45 sec at 0° C. after which time 300 μL of 20% aqueous acetonitrile +0.1% trifluoroacetic acid was added. The reaction mixture was immediately injected on a 25 cm Vydac C18 reversed-phase column equilibrated with 20% aqueous acetonitrile +0.1% trifluoroacetic acid. The column was washed under the same conditions for 10 min followed by a linear elution gradient (20 to 80% aqueous acetonitrile +0.1% trifluoroacetic acid) over 30 min. After the appearance of the peak corresponding to unreacted substrate 13, fractions of 250 μL were immediately collected and counted. The first peak of radioactivity following substrate 13 corresponded to the mono-labeled substrate 13a (Biotin-Arg-Gly-Tbg-Tbg-Asn(NMe)$_2$-Ala,Ser-Ser-Arg-Leu-Ala-Tyr($^{125}$I)-NH$_2$). These fractions were pooled and excess acetonitrile was evaporated. Casein, cold substrate 13, and dithiothreitol were added to the pool at a final concentration of 0.1% w/v, 20 μM and 5 mM respectively to prevent sticking and oxidation problems. Substrate 13a solution was stored in aliquots at 4° C. and was stable for 3–4 weeks.

EXAMPLE 7

Ac-Tbg-Tbg-Asn(Me)$_2$-Ala-pNP [SEQ ID NO: 8]

Neat POCl$_3$ (1.0 mL, 11 mmol) was added at −15° C. over 2 min. to a solution of Boc-Ala-OH (1.89 g, 10 mmol) and p-nitro aniline (1.38 g, 10 mmol) in pyridine (30 mL). The mixture was stirred for 30 min then it was poured into 100 mL of ice water and the resulting mixture was extracted with EtOAc (3×50 mL). The organic layers were combined and washed successively with 1M HCl (3×50 mL), saturated aqueous NaHCO$_3$ (3×50 mL) and saturated brine (3×50 mL). The organic layer was dried (Na$_2$SO$_4$) and the solvent was evaporated under reduced pressure. The residual solid was triturated with ether and filtered to give Boc-Ala-PNA as a yellow solid (1.72 g, 56% yield). $^1$H-NMR (DMSO-d6) 10.53 (s, 1H), 8.22 (d, J=10.5 Hz, 2H), 7.85 (d, J=9.2 Hz, 2H), 7.18 (broad d, J=6.3 Hz, 1H), 4.14 (t, J=7.0 Hz, 1H), 1.38 (s, 9H), 1.25 (d, J=7.0 Hz, 3H).

Starting from Boc-Ala-pNA and using a sequential deprotection and coupling protocol as described for example 4, the title compound was prepared as a white amorphous solid (after purification by semi-preparative HPLC). Electrospray-MS: MH$^+$=620.5 Da, Amino acid analysis: calc. (obs.) Asx 1 (0.96), Ala 1 (1.04), Tbg 2 (present, partial hydrolysis), Peptide recovery: 102+/−1%.

EXAMPLE 8

Ac-Tbg-Tbg-Asn(Me)$_2$-Ala-pNA [SEQ ID NO: 9]

The precursor Ac-Tbg-Tbg-Asn(Me)$_2$-Ala-OBn was synthesized in solution by an analogous process as the one described in example 4. The benzyl ester was hydrogenolyzed using a similar procedure as in example 1, Step B.

Starting from Ac-Tbg-Tbg-Asn(Me)$_2$-Ala-OH, the title compound was prepared according to the following protocol: The above tetrapeptide (200 mg, 0.4 mmol) and p-nitrophenol (60 mg, 0.43 mmol) were dissolved in DMF (2 mL) and EtOAc (5 mL). The mixture was cooled at 0° C. and a solution of DCC (80 mg, 0.388 mmol) in EtOAc (0.5 mL) was added. The mixture was stirred at 0° C. for 40 min. then at room temperature overnight. The mixture was filtered, the filtrate was diluted with EtOAc and was washed with aqueous saturated brine (2×10 mL) water (3×10 mL) and was dried (Na$_2$SO$_4$) to give, after evaporation of the solvent, 214 mg of a crude material which showed two peaks of roughly equal intensity by RP-HPLC. An attempt to purify the compound by chromatography on silica gel was made but no separation took place. All fractions were combined and were purified by semi-preparative HPLC (same chromatographic column and eluants as for example 3). Gradient: 0 to 20% eluant B/A in 10 min. then 20 to 60% eluant B/A in 80 min. Of the two compounds that were isolated, the slower moving one (A) was the desired compound (white amorphous solid, 40 mg), while the faster moving compound (B) was its corresponding D-Ala diastereomer (as determined on the digested peptide using a chiral GC column). Compound A: HPLC 100% homogeneity, Electrospray-MS: MH$^+$=621.4 Da, Amino acid analysis: calc. (obs.) Asx 1 (0.98), Ala 1 (1.02), Tbg 2 (1.29, partial hydrolysis), Peptide recovery: 90+/−8%.

EXAMPLE 9
Peptide-based ketoamide inhibitor
DA-Tbg-Tbg-Asn(Me$_2$)-Ala-CONHCH$_2$Ph [SEQ ID NO:4]

To a solution of nitroethane (4.0 g, 53 mmol) in ethanol (15 mL) was added aqueous NaOH (68 mL of 2N solution, 136 mmol). To this rapidly stirred solution was added glyoxylic acid (5.9 g, 64 mmol). The solution was stirred 15 h and then acidified with 10% aqueous HCl (pH 2) and the aqueous phase saturated with NaCl before extraction with EtOAc (3×150 mL). The organic phase was dried (MgSO$_4$), filtered and concentrated to give 8.1 g of a viscous yellow oil. This crude material was dissolved in ethanol (50 mL) containing Et$_3$N (18 mL, 119 mmol) and treated with di-tertiary-butyl dicarbonate (12.2 g, 56 mmol) and Raney nickel (3 g) which had been washed with water immediately before use. Hydrogenation at 45 p.s.i for 20 h afforded after filtration through diatomaceous earth and concentration, the crude acid (11.1 g). A portion of the crude acid (3.07 g, 14 mmol) was dissolved in DMF (30 mL) and treated with anhydrous K$_2$CO$_3$ (4.3 g, 30.8 mmol) and benzyl bromide (2.5 mL, 21 mmol). After stirring for 3 h at room temperature, the DMF was removed under reduced pressure and the residue dissolved in EtOAc (150 mL) and washed with water (100 mL) and brine (80 mL). The organic phase was dried over MgSO$_4$, filtered and concentrated. The crude yellow oil (4.3 g) was purified by flash chromatography on silica gel (230–400 mesh), eluting with 33% EtOAc in hexane to provide pure benzyl ester BocNHCH(Me)CHOHC(O)O-CH$_2$Ph (1.8 g, 42% from nitroethane). HPLC (system C) 99%, (system D) 97%; IR (KBr) v3422, 3361, 1740, 1684 cm$^{-1}$; $^1$H-NMR (400 MHz, CDCl$_3$) δ7.36 (s, 5H), 5.27 (d, J=12.1 Hz, 1H), 5.19 (d, J=12.1 Hz, 1H), 4.82 (m, 1H), 4.36 and 4.35 (2×d, J=5.7 and 5.4 Hz, 1H), 4.11 (m, 1H), 3.10 (m, 1H), 1.43 (s, 9H), 0.97 (d, J=7.0 Hz, 3H); FAB MS m/z: 310 (MH$^+$), 210 (M - 100); HRMS calcd for C$_{16}$H$_{24}$NO$_5$ (MH$^+$) 310.1654, found: 310.1644.

The tert-butyloxycarbonyl (Boc) group from the preceding benzyl ester (4.0 g, 12.9 mmol) was removed using 4 N HCl / dioxane (30 mL) for 45 min at 0° C. The hydrochloride salt was obtained by concentration and coevaporation with toluene (15 mL). The HCl salt (12.9 mmol) was combined with 1-ethyl-3-(3-dimethylaminopropyl) carbodiimide (2.6 g, 13.6 mmol, 1.1 equiv.), HOBT (1.8 g, 13.6 mmol, 1.1 equiv.) and Boc-Asn(NMe$_2$)-OH (3.4 g, 12.9 mmol, 1.1 equiv.) in DMF (50 mL) under a nitrogen atmosphere. The solution was cooled to 0° C. (ice bath) before iPr$_2$NEt (7.9 mL, 45.3 mmol, 3.5 equiv.) was added. The solution was then stirred at room temperature for 16 h. The reaction mixture was partitioned between EtOAc (250 mL) and sat. aqueous NaHCO$_3$ (150 mL). The organic phase was washed with 5% aq. HCl (150 mL) and finally brine (150 mL). Drying (MgSO$_4$) was followed by filtration and concentration to give 6.0 g of crude material. In most cases the crude material was suitable for subsequent couplings without purification. After the final coupling, the α-hydroxy benzyl ester peptide was purified by flash chromatography. The corresponding α-hydroxyacid was then obtained from the benzyl ester (1.10 g, 2.0 mmol) by hydrogenation over 10% Pd/C (55 mg) in ethanol (30 mL) at atmospheric pressure over the course of a few hours to afford after filtration through a pad of diatomaceous earth a white solid (0.95 g, 100% yield). HPLC (system A) 100%, (system C) 100%; IR (KBr) v3316, 1727, 1642 cm$^{-1}$; $^1$H-NMR (400 MHz, CDCl$_3$), mixture of 4 diastereomers, δ8.06 and 8.01 (2×d, J=7.3 and 8.6 Hz, 1H), 7.87, 7.79, 7.70 and 7.54 (4x d, J=8.6, 8.6, 8.9 and 8.6 Hz, 1H), 7.09 and 7.03 (2 x d, J =7.9 and 8.6 Hz, 0.5H), 6.72 (m, 0.5H), 6.52 (m, 0.25), 6.34 and 6.29 (2×d, J=7.6 and 7.3 Hz, 0.75H), 6.10-5.4 (br s, 1H), 4.99-4.88 (m, 0.5H), 4.87-4.78 (m, 0.5H), 4.66-4.37 (m, 2H), 4.33-4.09 (m, 1H), 3.30-3.15 (m, 0.3H), 3.05-2.85 (m, 6.7H), 2.75-2.65 and 2.60-2.50 (m, 1H), 2.25-2.10 (m, 2H), 1.28-1.19 (m, 3H), 1.10-0.97 (m, 18H); $^{13}$C-NMR (100.6 MHz, CDCl$_3$) d 174.9, 173.5, 173.1, 173.0, 171.5, 171.0, 170.9, 170.8, 170.7, 170.5, 170.2, 73.03, 72.74, 60.9, 60.67, 50.3, 50.1, 49.5, 49.4, 48.1, 47.9, 47.7, 37.56, 35.9, 35.8, 35.7, 34.7, 34.4, 34.3, 33.8, 31.1, 29.9, 29.8, 26.9, 26.8, 26.7, 17.4, 17.2; FAB MS m/z: 473 (MH$^+$), 495 (M+23). Coupling of the P$_1$' residue was accomplished using the above general coupling protocol with benzylamine (1.2 equiv.). The final oxidation step was performed by treatment of the prerequisite α-hydroxy amide (62 mg, 0.11 mmol) with 2 equivalents of 1,1,1-triacetoxy-1,1-dihydro-1,2-benziodoxol-3(1H)-one (94 mg, 0.22 mmol) in DMF (1 mL) for 4 h. Addition of 10% sodium thiosulfate (5 mL) and sat. NaHCO$_3$ (5 mL) with stirring (15 min) was followed by extraction with EtOAc (3×10 mL) to give the desired α-ketoamide. Final purification was performed using preparative HPLC to afford after lyophilization DATbg-Tbg-Asn(Me$_2$)-Ala-C(O)NHCH$_2$Ph, (51 mg, 82% yield) as a white solid. HPLC (system C) 100%, (system D) 96.1%; IR (KBr) U 3316, 1641, 1529 cm$^{-1}$; $^1$H-NMR (400 MHz, DMSO-d$_6$), 1:1 mixture of diastereoisomers at P$_1$,δ9.21-9.15 (m, 1H), 8.14 and 8.09 (2×d, 7.3 and 7.6 Hz, 1H), 8.03 and 7.97 (2×d, J=6.4 and 5.7 Hz, 1H), 7.60 (d, J=8.3, 1H), 7.35-7.17 (m, 5H), 5.02-4.88 (m, 1H), 4.64-4.49 (m, 1H), 4.39-4.23 (m, 2H), 4.13 and 4.12 (2×d, J=8.6 and 8.6 Hz, 1H), 2.92 and 2.91 (2×s, 3H), 2.79 and 2.78 (2×s, 3H), 2.74-2.54 (m, 2H), 2.19 (br d, J=12.4 Hz, 1H), 2.03 and 2.02 (2×d, J=12.4 and 12.7 Hz, 1H), 1.25 and 1.23 (2×d, J=7.3 and 7.0 Hz, 3H), 0.94 and 0.91 (2×s, 18H); FAB MS m/z: 560 (MH+), 582 (M+23).

EXAMPLE 10

HCMV protease assay

Stock solutions (10 mM) in DMSO of the compounds prepared in examples 2, 3, 4, 5 and 6 were stored at 4° C. The compounds in these solutions were stable for several weeks under these conditions. Aliquoted samples of HCMV protease 50 μM (1.4 mg/ml) were kept at −80° C. in storing buffer without detectable loss of activity over an extended period of more than a year. The calculated molecular mass of wild-type HCMV protease was 28042 Da. The concentration of enzyme on which the calculations of the turnover number, $k_{cat}$, and the specificity constant, $k_{cat}/K_m$, were derived was expressed in terms of total monomer concentration.

HPLC analysis. Specificity constant, $k_{cat}/K_m$, and individual parameters $k_{cat}$ & $K_m$ for the peptide substrate of Example 2 were determined by HPLC monitoring of the initial rate of appearance of the N-terminus cleavage product at various substrate concentrations. Incubation buffer contained 50 mM Tris/HCl pH 8, 0.5 M Na$_2$SO$_4$, 50 mM NaCl, 0.1 mM EDTA, 1 mM TCEP, 3% DMSO v/v, & 0.05% w/v casein to which 20-500 μM substrate was added. Following equilibration at 30° C., the reactions were initiated by addition of 50 nM HCMV protease (total monomer concentration) from a 2.5 μM stock solution in assay buffer and quenched at regular intervals with 1% TFA up to ≈25% total hydrolysis. The aliquots were injected on a C8 reversed-phase column using a linear gradient of acetonitrile in aqueous 3mM SDS containing 0.05% H$_3$PO$_4$ (22 to 28% acetonitrile at 2 min, to 30% at 4 min, to 50% at 6 min at a constant flow rate of 4 ml/min). A calibration curve of the N-terminus product was used to estimate the extent of the conversion (retention time=2.7 min). The data was fitted to the non-linear regression analysis of the Michaelis-Menten equation by the kinetic software GRAFIT (Grafit, Erithacus Software Ltd, 1989–1992, Version 3.0, Leatherbarrow, R. J., London, U.K.). A similar protocol was adopted for the peptide substrates of Examples 5 and 6. In this case the enzyme concentration used was respectively 500 nM and 200 nM. The HPLC gradient was 25 to 38% acetonitrile at 11 min, to 100% at 13 min at a constant flow rate of 4 ml/min.

Fluorometric assay. Specificity constant, $k_{cat}/K_m$, and individual parameters $k_{cat}$ & $K_m$ for the peptide substrates of Example 3 and 4 were determined by initial rate kinetics as measured from the increase in fluorescence intensity upon cleavage of the Ala-Ser or Ala-AMC amide bond in presence of 50 nM HCMV protease (for anthranilamide $\lambda_{ex}$=312 nm & $\lambda_{em}$=415 nm, for 7-amino-4-methylcoumarin $\lambda_{ex}$=360 nm & $\lambda_{em}$=440 nm. Slit width sizes varied from 2.5 nm to 5 nm).

Substrate concentrations above and below $K_m$ were used to accurately determine the individual kinetic parameters. Reaction conditions and data fitting were as described above.

Radiometric assay: The utility of this optimized sequence Tbg-Tbg-Asn(Me)$_2$ was not limited to fluorogenic substrates and could be successfully applied to other methodologies. Indeed, introduction of this sequence into the radiometric substrate having the structure of formula 12a:

d-Biotin-Arg-Gly-Val-Val-Asn-Ala-Ser-Ser-Arg-Leu-Ala-Tyr($^{125}$,)-NH$_2$ (12a) [SEQ ID NO: 6]

led to the substrate having the structure of formula 13a:

d-Biotin-Arg-Gly-Tbg-Tbg-Asn(Me)$_2$-Ala-Ser-Ser-Arg-Leu-Ala-Tyr($^{125}$,)-NH$_2$ (13a) [SEQ ID NO:7]

whose $k_{cat}$ & $K_M$ values of 0.045 s$^{-1}$ and 19 μM respectively led to a specificity constant, $k_{cat}/K_M$, of 2370 M$^{-1}$s$^{-1}$ i.e. 12-fold greater compared to the substrate of formula 12a (as measured by HPLC). These kinetic improvements permitted the conversion of a standard radiometric assay into a Scintillation Proximity Assay {Bosworth, N., Towers, P. (1989) Nature 341, 167-8; and Brown, A. M., George, S. M., Blume, A. J., Dushin, R. G., Jacobsen, J. S., Sonneberg-Reines, J. (1994) Anal. Biochem. 217, 139–147} with the considerable advantages of reducing enzyme concentration, incubation time and manipulations. This assay, based on $^{125}$I, compares favorably to the HCMV protease SPA already published which requires a longer substrate and the use of protein Kinase A for phosphorylation with $^{33}$p {Baum, E.Z., Johnston, S. H., Bebernitz, G. A., Gluzman, Y. (1996), Anal. Biochem. 237, 129–134}.

Chromogenic assay: Kinetic parameters ($k_{cat}$, $K_m$ and $k_{cat}/K_m$) for the calorimetric peptide substrates of Example 7 and 8 are determined by initial rate kinetics as measured from the increase in absorbance at λ=405 nm upon cleavage of the p-nitrophenol or p-nitroaniline moiety in presence of HCMV protease. Substrate concentrations above and below $K_m$ can be used to accurately determine the individual kinetic parameters. Reaction conditions and data fitting are as described above.

Hence, the synthesis and characterization of improved substrates for HCMV protease have been described. The improvements were based on the replacement of the P$_4$–P$_2$ Val-Val-Asn sequence of previous substrates by the modified amino acids Tbg-Tbg-Asn(Me)$_2$ identified during QSAR studies of inhibitors. These modifications, shown to significantly increase potency of peptide-based inhibitors, were successfully transposed into substrates and translated into lower $K_m$ and faster second-order rates of cleavage. These improved substrates (the substrate of formula 2 and the substrate of formula 3) led to the development of low nanomolar enzyme assays for unambiguous characterization of potent HCMV protease inhibitors and to the expansion of kinetic fluorescence applications not possible with the currently available fluorogenic substrates. The kinetic characterization of HCMV protease mutants displaying lower activity than the wild type enzyme is also expected to be greatly enhanced. Although the absolute kinetic parameters can vary depending on the enzyme preparation and the experimental conditions, the relative improvements described in this work are likely to be conserved. This strategy can also be successfully applied to other detection methods. An improved HPLC, radiometric and chromogenic HCMV protease substrate (the substrate of formula 13a) has been prepared which allow for rapid and convenient assays including the scintillation proximity approach. {Bosworth, N. et al., vide infra; Brown, A. M. et al.,vide infra; and Baum, E. Z. et al., vide infra.}

What is claimed is:

1. A substrate, suitable for cleavage by a cytomegalovirus protease, represented by formula I X-Tbg-Tbg-Y-Ala-Z (I) [SEQ ID NO: 1]

wherein X is a fluorescent donor radical, a fluorescent acceptor radical, an affinity tag, a detectable label or an N-terminal capping group, or X is an amino acid sequence sufficient for substrate recognition and to which a fluorescent donor radical, a fluorescent acceptor radical, an affinity tag, a detectable label or an N-terminal capping group, is optionally attached;

Y is NHCH{CH$_2$C(O)N(R$^1$)(R$^2$)}C(O) wherein R$^1$ and R$^2$ are independently selected from hydrogen, lower alkyl, lower cycloalkyl, or lower cycloalkyl-lower alkyl or R$^1$ and R$^2$ together with the nitrogen atom to which they are attached form a pyrrolidino, piperidino or morpholino,; and Z is an amino acid sequence sufficient for substrate recognition and to which a fluorescent donor radical, a fluorescent acceptor radical, an affinity tag or a detectable label is optionally attached; or Z is a radical derived from an aromatic amino or phenoxy compound whose fluorescence or absorbance characteristics change upon acylation with an amino acid; or Z is amino, lower alkylamino or lower alkoxy; with the provisos (1) that when one of X and Z comprises a fluorescent donor radical then the other of X and Z comprises a fluorescent acceptor radical, and (2) that when one of X and Z comprises an affinity tag then the other of X and Z comprises a detectable label; wherein said protease cleaves the substrate at the corresponding amide or ester bond between Ala and Z.

2. The substrate of claim 1 wherein Z is an aromatic amino or phenoxy radical derived by removal of a hydrogen from the appropriate amino group or hydroxyl, respectively, of 7-amino-4-methylcoumarin; 6-amino-1-naphthalenesulfonamide; rhodamine 110; 2-naphthylamine; 4-methoxy-2-naphthylamine; 4-nitroaniline; or 4-nitrophenol.

3. The substrate of claim 1 which comprises covalent linkages to a fluorescent donor radical and a fluorescent acceptor radical, said donor and acceptor radicals being separated by the alanine residue and 7 to 12 additional amino acid residues.

4. The substrate of claim 3 wherein the fluorescent donor radical is selected from 2-aminobenzoyl and halogenated derivatives thereof; 5-{(2-aminoethyl)amino}naphthalene-1-sulfonyl;5-dimethylaminonaphthalene-1-sulfonyl; 7-methoxycoumarin-4-acetyl; nicotinic acid and derivatives thereof; and tryptophan; and the fluorescent acceptor radical is selected from 3-nitrotyrosine; 4-nitrophenylalanine; 2,4- dinitrophenylalanine; 5-(dimethylamino)naphthalene-1-sulfonyl; 4-{{4-(dimethylamino)phenyl}azo}benzoyl; or 4-(dimethylamino)azobenzene-4'-sulfonyl.

5. The substrate of claim 3 wherein the donor/acceptor pairs are selected from the group consisting of:

EDANS/DABCYL;

tryptophan/2,4-dinitrophenyl;

tryptophan/dansyl;

7-methoxycoumarin/2,4-dinitrophenyl;

2-aminobenzoyl/2,4-dinitrophenyl; and 2-aminobenzoyl/3-nitrotyrosine.

6. The substrate of claim 1 wherein said substrate comprises a linkage to a detectable label.

7. The substrate of claim 6 wherein said detectable label is selected from a radioactive label or an indicator molecule.

8. The substrate of claim 1 wherein said substrate comprises linkages to a detectable label and an affinity tag.

9. The substrate of claim 8 wherein said detectable label is selected from $^{125}$I or β-galactosidase and said affinity tag is selected from biotin or a derivative thereof; a polyhistidine; an amylose sugar radical; or a defined epitope recognizable by a specific antibody.

10. The substrate of claim 1 wherein the N-terminal capping group is selected from acetyl or succinimidyl.

11. The substrate of claim 1 having the structure of ABz-Tbg-Tbg-Asn(Me)$_2$-Ala-Ser-Ser-Arg-Leu-Tyr(3-NO$_2$)-Arg-OH. [SEQ ID NO.: 2]

12. The substrate of claim 1 having the structure of N-acetyl-Tbg-Tbg-Asn(Me)$_2$-Ala-AMC.

13. The substrate of claim 1 having the structure d-Biotin-Arg-Gly-Tbg-Tbg-Asn(Me)$_2$-Ala-Ser-Ser-Arg-Leu-Ala-Tyr-NH$_2$. [SEQ ID NO: 4]

14. The substrate of claim 13, wherein said substrate is labeled with $^{125}$I.

15. The substrate of claim 1 having the structure Ac-Tbg-Tbg-Asn(Me)$_2$-Ala-pNP.

16. The substrate of claim 1 having the structure Ac-Tbg-Tbg-Asn(Me)$_2$-Ala-pNA.

17. A method of measuring the activity of a cytomegalovirus protease comprising the steps of contacting said cytomegalovirus protease with a substrate as defined in claim 1, 11, or 12; and monitoring the cleavage of said substrate.

18. The method of claim 17 wherein the step of monitoring the cleavage of said substrate comprises determining a change in the size of the said substrate.

19. The method of claim 17 wherein the step of monitoring the cleavage of said substrate comprises determining a change in fluorescence or absorbance of the substrate upon cleavage of the substrate.

20. The method of claim 17 wherein the step of monitoring the cleavage of said substrate comprises determining a change in solvent extractability of the detectable label.

21. A method of identifying an inhibitor of a cytomegalovirus protease comprising the steps of: (1) contacting said cytomegalovirus protease with a substrate as defined in claim 1, 11, or 12 in the presence of a test compound; and (2) monitoring the cleavage of said substrate to determine the level of inhibition of the activity of the protease caused by said test compound.

22. The method of claim 21 wherein the step of monitoring the cleavage of said substrate comprises determining a change in size of the said substrate.

23. The method of claim 21 wherein the step of monitoring the cleavage of said substrate comprises determining a change in fluorescence or absorbance of the substrate upon cleavage of the substrate.

24. The method of claim 21 wherein the step of monitoring the cleavage of said substrate comprises determining a change in solvent extractability of the detectable label.

25. A kit for measuring the activity of a cytomegalovirus protease comprising: a cytomegalovirus protease, and a substrate as defined in claim 1, 11, or 12.

26. The substrate of claim 7, wherein said indicator molecule is β-galactosidase.

* * * * *

```
                         SEQUENCE LISTING

<160> NUMBER OF SEQ ID NOS: 4

<210> SEQ ID NO 1
<211> LENGTH: 11
<212> TYPE: PRT
<213> ORGANISM: Artificial Sequence
<220> FEATURE:
<221> NAME/KEY: PEPTIDE
<222> LOCATION: (1)
<223> OTHER INFORMATION: Modified-site:  Xaa at position 1 is
      aminobenzoic acid
<220> FEATURE:
<221> NAME/KEY: PEPTIDE
<222> LOCATION: (10)
<223> OTHER INFORMATION: Modified-site:  Xaa at position 10 is 3-nitro
      tyrosine
<220> FEATURE:
<223> OTHER INFORMATION: Description of Artificial Sequence:Substrates
      for HCMV protease

<400> SEQUENCE: 1

Xaa Val Val Asn Ala Ser Ser Arg Leu Xaa Arg
 1               5                  10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence:SUBSTRATES
      FOR HCMV PROTEASE
<220> FEATURE:
<221> NAME/KEY: PEPTIDE
<222> LOCATION: (1)
<223> OTHER INFORMATION: Xaa at position 1 is aminobenzoic acid
<220> FEATURE:
<221> NAME/KEY: PEPTIDE
<222> LOCATION: (2)
<223> OTHER INFORMATION: Xaa at position 2 is Tbg
<220> FEATURE:
<221> NAME/KEY: PEPTIDE
<222> LOCATION: (3)
<223> OTHER INFORMATION: Xaa at position 3 is Tbg
<220> FEATURE:
<221> NAME/KEY: PEPTIDE
<222> LOCATION: (4)
<223> OTHER INFORMATION: Xaa at position 4 is dimethyl-asparagine
<220> FEATURE:
<221> NAME/KEY: PEPTIDE
<222> LOCATION: (10)
<223> OTHER INFORMATION: Xaa at position 10 is 3-nitro tyrosine

<400> SEQUENCE: 2

Xaa Xaa Xaa Xaa Ala Ser Ser Arg Leu Xaa Arg
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence:Substrates
      for HCMV protease
<220> FEATURE:
<221> NAME/KEY: PEPTIDE
<222> LOCATION: (1)
<223> OTHER INFORMATION: Label=X: X is biotin
```

-continued

```
<220> FEATURE:
<221> NAME/KEY: PEPTIDE
<222> LOCATION: (12)
<223> OTHER INFORMATION: C-Terminal is replaced (note: carboxyl group
      at C-terminal replaced by NH2)

<400> SEQUENCE: 3

Arg Gly Val Val Asn Ala Ser Ser Arg Leu Ala Tyr
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence:Substrates
      for HCMV protease
<220> FEATURE:
<221> NAME/KEY: PEPTIDE
<222> LOCATION: (1)
<223> OTHER INFORMATION: Label=X:  X is d-Biotin
<220> FEATURE:
<221> NAME/KEY: PEPTIDE
<222> LOCATION: (3)
<223> OTHER INFORMATION: Xaa at position 3 is Tbg
<220> FEATURE:
<221> NAME/KEY: PEPTIDE
<222> LOCATION: (4)
<223> OTHER INFORMATION: Xaa at position 4 is Tbg
<220> FEATURE:
<221> NAME/KEY: PEPTIDE
<222> LOCATION: (5)
<223> OTHER INFORMATION: Xaa at position 5 is dimethyl asparagine
<220> FEATURE:
<221> NAME/KEY: PEPTIDE
<222> LOCATION: (12)
<223> OTHER INFORMATION: COOH at C-Terminal is replaced by NH2

<400> SEQUENCE: 4

Arg Gly Xaa Xaa Xaa Ala Ser Ser Arg Leu Ala Tyr
 1               5                  10
```